(12) United States Patent
Stahnke (10) Patent No.: US 10,362,796 B2
(45) Date of Patent: *Jul. 30, 2019

(54) METHOD FOR REDUCING THE CONTENT OF PATHOGENIC ORGANISMS PRESENT IN FOOD MATERIALS

(71) Applicant: Chr. Hansen A/S, Hoersholm (DK)

(72) Inventor: Marie Louise Heller Stahnke, Virum (DK)

(73) Assignee: CHR. HANSEN A/S, Hoersholm (DK)

( * ) Notice: Subject to any disclaimer, the term of this patent is extended or adjusted under 35 U.S.C. 154(b) by 96 days.

This patent is subject to a terminal disclaimer.

(21) Appl. No.: 15/359,197

(22) Filed: Nov. 22, 2016

(65) Prior Publication Data
US 2017/0071237 A1 Mar. 16, 2017

Related U.S. Application Data (63) Continuation of application No. 14/444,285, filed on Jul. 28, 2014, now Pat. No. 9,504,276, which is a continuation of application No. 13/290,578, filed on Nov. 7, 2011, now Pat. No. 8,828,459, which is a continuation of application No. 11/578,331, filed as application No. PCT/DK2005/000259 on Apr. 15, 2005, now abandoned.

(30) Foreign Application Priority Data

Apr. 15, 2004 (DK) .................................. 2004 00596

(51) Int. Cl.
| | | |
|---|---|---|
| *A23L 13/40* | (2016.01) | |
| *A23L 3/3571* | (2006.01) | |
| *C12N 1/20* | (2006.01) | |
| *C12R 1/01* | (2006.01) | |

(52) U.S. Cl.
CPC ............ *A23L 13/45* (2016.08); *A23L 3/3571* (2013.01); *C12N 1/20* (2013.01); *C12R 1/01* (2013.01); *A23V 2002/00* (2013.01); *A23Y 2220/77* (2013.01)

(58) Field of Classification Search
CPC .......... A23L 13/45; A23L 3/3571; C12N 1/20
USPC ...................................................... 426/90, 92
See application file for complete search history.

(56) References Cited

U.S. PATENT DOCUMENTS

| | | | | |
|---|---|---|---|---|
| 4,238,513 | A | 12/1980 | Satz | |
| 4,303,679 | A | 12/1981 | Raccach | |
| 5,186,962 | A | 2/1993 | Hutkins et al. | |
| 8,828,459 | B2 * | 9/2014 | Stahnke | C12R 1/01 426/335 |
| 9,504,276 | B2 * | 11/2016 | Stahnke | C12R 1/01 |
| 2004/0208978 | A1 | 10/2004 | Jiang et al. | |
| 2005/0106662 | A1 | 5/2005 | Devuyst et al. | |
| 2008/0102159 | A1 | 5/2008 | Stahnke | |
| 2012/0114790 | A1 | 5/2012 | Stahnke | |

FOREIGN PATENT DOCUMENTS

| | | |
|---|---|---|
| DK | 9400266 U4 | 6/1994 |
| EP | 0 776 611 A1 | 6/1997 |
| WO | WO-2005/100614 A1 | 10/2005 |

OTHER PUBLICATIONS

Foegeding et al. Appl. Environ. Microbiol. 58: 884-890 (1992) (Year: 1992).*
"B-LC-20 La nouvelle solution de Chr. Hansen dans la lutte contre Listeria," Process, Oct. 2004, 1 page.
A. Amezquita et al., "Competitive Inhibition of Listeria monocytogenes in Ready-To-Eat Meat Products by Lactic Acid Bacteria", Journal of Food Production, 65(2): 316-215 (Feb. 2002).
American Meat Institute Foundation, "The Science of Meat and Meat Products," W.H. Freeman and Company, 1960, 3 pages.
Chr. Hansen A/S, "B-LC-20 SafePro Product Information," retrieved www.chr-hansen.com, Dec. 2004, 2 pages.
Chr. Hansen A/S, "Reduction of Listeria in fermented dried sausage with B-LC-20 SafePro™" Retrieved from www.chr-hansen.com, Dec. 2004, 2 pages, XP002337954.
Community Register of Feed Additives, Nov. 2007, retrieved from ec.europa.eu/comm/food/food/animalnutrition/feedadditives/ registeradditives_en.htm, 2 pages.
Danisco Cultor Niebull GmbH, "BioCarna meat cultures," Mar. 2001-GES/BIK. pp. 1-8.
E. Lahti et al., "Survival and detection of *Escherichia coli* O157:H7 and Listeria monocytogenes during the manufacture of dry sausage using two different starter cultures," Food Microbiology, 18(1):75-85 (Feb. 2001).
Erol et al., Effect of Bacteriocinogenic Starter Culture on the Growth of Listeria monocytogenes in Turkish Fermented Sausage (Sucuk), Ek Sayi 4, 23:793-802 (Jan. 1999).
Hugas et al., "Inhibition of Listeria in dry fermented sausages by bacteriocinogenic Lactobacillus sake CTC494," J Appl. Bacteriol. 79: 322-30, (1995).
International Search Report dated Aug. 11, 2005 issued in International Application No. PCT/DK2005/000259.

(Continued)

*Primary Examiner* — Hamid R Badr
(74) *Attorney, Agent, or Firm* — Foley & Lardner LLP (57) ABSTRACT

The present invention relates to a method for reducing the concentration of pathogenic organisms such as *Listeria* spp. in fermented food products. The method comprises the steps of: (i) providing a food material, (ii) mixing said food material with a starter culture, (iii) mixing the food material with at least one adjunct culture in form of a bacteriocin-producing *Pediococcus* species, (iv) subjecting the mixture provided in step (iii) to a fermentation process, said fermentation process being con-ducted at conditions that are sub-optimal for growth of the bacteriocin-producing *Pediococcus* species in order to provide a limited acidification and allow for a high production of bacteriocin, and obtain a fermented food product. Furthermore, the invention relates to the use of bacteriocin-producing *Pediococcus* species as an adjunct culture for securing microbial safety of fermented food products.

17 Claims, 4 Drawing Sheets

(56) References Cited

OTHER PUBLICATIONS

K. Tjener et al., "A fermented meat model system for studies of microbial aroma formation", Meat Science, 66:211-218 (Apr. 2003).

Kureha Chem Ind Co Ltd., JP 62 0911 63-A— Apr. 25, 1987, Database WPI, Derwent Publications Ltd., Abstract, XP-002338088.

Lau, Zhan-li; Studies on Production Technology and Physico-Chemical Microbial Changes During the Processing of Fermented Sausage; pp. 1-57 (Jun. 2003) (with English abstract).

Leroy et al., "Lactic acid bacteria as functional starter cultures for the food fermentation industry", Trends in Food Science & Technology, 15(2):67-78 (Feb. 2004).

Mataragas et al., "Influence of pH and temperature on growth and bacteriocin production by Leuconostoc mesenteroides L 124 and Lactobacillus curvatus L442", Meat Science, 64(3):265-271 (Jul. 2003).

U.S. Office Action issued in U.S. Appl. No. 13/290,578 (US 2012-0114790) dated Jan. 16, 2014.

Office Action dated Jul. 11, 2008, in Chinese Application No. 200580010927.2.

O'Sullivan, "Potential of bacteriocin-producing lactic acid bacteria for improvements in food safety and quality," Biochimie, 84(5-6):593-604 (Jul. 2002).

Foegeding et al., "Enhanced Control of Listeria monocytogenes by In Situ-Produced Pediocin during Dry Fermented Sausage Production", Applied and Environmental Microbiology, 58(3):884-890 (Mar. 1992).

Rhodia Foods, "Texel Dried CC-430 Product Technical Data Sheet", Mar. 2003, 2 pages.

The Lactic Acid Bacteria: The Genera of Lactic Acid Bacteria 158 (B.L.B. Wood & W.H. Holzapfel eds., 1st ed. 1995).

U.S. Notice of Allowance issued in U.S. Appl. No. 13/290,578 (US 2012-0114790) dated Jun. 20, 2014.

U.S. Notice of Allowance issued in U.S. Appl. No. 14/444,285 (US 2015-0024086) dated Aug. 2, 2016.

U.S. Office Action issued in U.S. Appl. No. 11/578,331 (US 2008-0102159) dated Mar. 30, 2010.

U.S. Office Action issued in U.S. Appl. No. 11/578,331 (US 2008-0102159) dated May 10, 2011.

U.S. Office Action issued in U.S. Appl. No. 11/578,331 (US 2008-0102159) dated Oct. 27, 2010.

U.S. Office Action issued in U.S. Appl. No. 13/290,578 (US 2012-0114790) dated May 10, 2013.

U.S. Office Action issued in U.S. Appl. No. 13/290,578 (US 2012-0114790) dated Sep. 20, 2012.

U.S. Office Action issued in U.S. Appl. No. 14/444,285 (US 2015-0024086) dated Nov. 18, 2015.

Written Opinion dated Aug. 11, 2005 issued in International Application No. PCT/DK2005/000259.

\* cited by examiner

METHOD FOR REDUCING THE CONTENT OF PATHOGENIC ORGANISMS PRESENT IN FOOD MATERIALS

CROSS-REFERENCE TO RELATED PATENT APPLICATIONS

This application is a Continuation of U.S. application Ser. No. 14/444,285, filed Jul. 28, 2014, which is a Continuation of U.S. application Ser. No. 13/290,578, filed Nov. 7, 2011 (now U.S. Pat. No. 8,828,459), which is a Continuation of U.S. application Ser. No. 11/578,331 filed Aug. 6, 2007 (now abandoned), which is the U.S. National Stage of International Application PCT/DK2005/000259 filed Apr. 15, 2005, which claims the benefit of Denmark Patent Application No. 200400596 filed Apr. 15, 2004. The entire disclosures of the U.S. and P.C.T. applications are incorporated herein by reference.

FIELD OF INVENTION

The present invention relates to the field of improving microbial safety in the production of food products. In particular the present invention relates to microbial strains useful for reducing the amount of pathogenic organisms e.g. *Listeria* when added to a fermented food products, such as a fermented meat product

PRIOR ART

During the production of fermented food products, such as e.g. sausage products, a starter culture is most often applied in order to control the fermentation process instead of relying on the natural developing flora. Commonly, the starter culture comprises a combination of one or more lactic acid bacteria (LAB) and one or more species from the *Micrococcaceae* and *Staphylococcaceae* families. During the fermentation process the lactic acid bacteria primarily produce lactic acid whereby pH drops to the desired pH-value depending on the culture and the processing conditions (temperature, sugar type/content etc.) and the food product produced.

Whereas the lactic acid bacteria are mainly responsible for the acid formation, the *Micrococcaceae* spp. and *Staphylococcaceae* spp. are responsible for enhancing the flavour formation by producing non-volatile and volatile compounds through various biochemical reaction steps. Additionally, the *Micrococcaceae* spp. and *Streptococcaceae* spp. are responsible for the speed and intensity of colour formation in particular in fermented sausage types.

*Micrococcaceae* spp. and *Streptococcoceae* spp. are very sensitive to low pH as their growth is drastically slowed down when pH is reduced to a pH below 5.0. In e.g. the manufacturing of dried sausages it is essential for the flavour and colour formation of the meat products that the acidification profile is well-controlled and is not altered from batch to batch. In particular, a fast pH-lowering may impair the quality and result in a less mature and less complex flavour profile that will force the food product manufacturer to ripen the food product for a longer period of time to reach the same flavour intensity (Tjener et al., 2003).

In manufacturing of fermented food products presence of pathogenic organisms like *Listeria monocytogenes* may be a problem if the raw materials are contaminated. During the production of e.g. fermented sausages *Listeria monocytogenes* will normally decrease in numbers during the fermentation and ripening period, primarily, due to the formation of lactic acid, the resulting drop in pH and due to the reduction in water activity caused by the subsequent drying process. However, quite often, a considerable number of *Listeria monocytogenes* survives. This may cause a serious safety problem as consumption of infected food may give rise to lethal listerial infections (listeriosis).

In order to reduce the presence of pathogenic microorganisms in the food product certain bacteriocin producing lactic acid bacteria including *Pediococcus* strains and certain *Lactobacillus* strains have been added to the starter culture to produce bacteriocins some of which kill and/or inactivate the pathogenic organisms and accordingly reduce their concentration in the product.

Foegeding et al. (1992) disclose the effectiveness of pediocin produced in situ by *Pediococcus acidilactici* as an antilisterial component. However, the fermentation of sausages was conducted at 38° C. which caused an extensive acid production and thus a very fast drop in pH. As mentioned above a rapid pH-lowering impairs the general quality of the product and results in a less mature and less complex flavoured profile. Thus, the adverse influence of *Pediococcus acidilactici*, on the general quality of the resulting product renders the method unsuitable for food fermentations where the above-mentioned conditions and features apply.

Utility model BA 1994 00266 discloses a lactic acid bacterial starter culture comprising a selected bacteriocin-producing *Pediococcus* spp. and a selected bavaricin-producing *Lactococcus* useful for inhibiting pathogenic organisms e.g. *Listeria* in meat products including fermented meat products.

Evidently, *Pediococcus* spp. are often not well qualified as starter cultures in the manufacturing of food products although the species are known for their potential for reducing the amount of pathogenic organisms e.g. *Listeria*.

Thus, there is a persisting need in the industry to be able to reduce the amount of pathogenic organisms and at the same time obtain optimal characteristics of the fermented food product e.g. acidification profile, flavour and colour development.

SUMMARY OF THE INVENTION

Accordingly, in interesting aspects, methods for A) manufacturing of a fermented food product and B) for reducing the concentration of *Listeria* spp (in particular *Listeria monocytogenes* in a fermented food product are provided. Said methods comprise the steps of:
  (i) providing a food material,
  (ii) mixing the food material with a starter culture,
  (iii) mixing the food material with at least one adjunct culture in form of a bacteriocin-producing *Pediococcus* species,
  (iv) subjecting the mixture obtained in step (iii) to a fermentation process, said fermentation process being conducted at conditions that are sub-optimal for growth of the bacteriocin-producing *Pediococcus* species in order to provide a limited acidification and allow for a high production of bacteriocin, and obtain the fermented food product.

In another aspect of the present invention a fermented food product obtainable by a method of the present invention is provided.

In a further aspect, the present invention provides, bacteriocin-producing *Pediococcus* species for use as an adjunct culture for securing microbial safety of a fermented food product, wherein said culture, when added to a food fermentation process, is being subjected to conditions that are sub-optimal for growth of said species, thereby producing bacteriocin without significantly affecting the acidification profile of the fermentation.

DETAILED DISCLOSURE

Prior to a discussion of the detailed aspects and embodiments of the invention a definition of specific terms used herein is provided.

As used herein, the term "fermentation" or "food fermentation" refers to the process of biochemical changes e.g. an acidification in animal and/or plant material (i.e. a food matrix), involving activity of live microbial cells under aerobic and/or anaerobic conditions to obtain a food product of desired quality.

The term "adjunct culture" is to be understood as a microbial culture that can be added to a food matrix and produce a bacteriostatic and/or bacteriocritic product (e.g. bacteriocins and antibiotics) without adversely affecting the desired fermentation profile of said food matrix. Preferably, the adjunct culture does not adversely affect the acidification profile during manufacturing of the food product.

It follows that "conditions sub-optimal for growth" are to be understood as growth conditions allowing the adjunct culture, when added to the food matrix, to act as described above.

The term "starter culture" refers to a preparation containing microbial cells that is intended for inoculating a food matrix to be subjected to fermentation. The starter culture is intended for providing the desired change in the characteristics of the food matrix during fermentation (e.g. a desired acidification). Typically, a starter culture will proliferate during the fermentation process.

A "bioprotective agent" is to be understood as a live organism that exerts its bioprotective effect when added to a food matrix without adversely affecting the food matrix.

The bioprotective effect is defined as an effect accomplished by the production of a bacteriostatic and/or bacteriocritic product whereby the presence and/or activity of undesired organisms e.g. *Listeria monocytogenes* is inhibited and/or diminished.

In the present context, the term "microorganism" is used in its normal meaning. Thus, in its broadest meaning the term "microorganism" is intended to cover algae, protozoa, viruses, bacteria and fungi. Preferred microorganisms are bacteria and fungi, in particular bacteria, such as lactic acid bacteria.

The expression "lactic acid bacteria (LAB)" designates a group of Gram positive, catalase negative, non-motile, microaerophilic or anaerobic bacteria which ferment sugar with the production of acids including lactic acid as the predominantly produced acid, acetic acid, formic acid and propionic acid. The industrially most useful lactic acid bacteria are found among *Lactococcus* species, *Streptococcus* species, *Enterococcus* species, *Lactobacillus* species, *Leuconostoc* species, *Pediococcus* species and *Bifidobacterium* species.

Commonly used starter culture strains of lactic acid bacteria are generally divided into mesophilic organisms having optimum growth temperatures at about 30° C. and thermophilic organisms having optimum growth temperatures in the range of about 40 to about 45° C. Typical organisms belonging to the mesophilic group include *Lactococcus lactis, Lactococcus lactis* subsp. *cremoris, Leuconostoc mesenteroides* subsp. *cremoris, Pediococcus pentosaceus, Lactococcus lactis* subsp. *lactis* biovar. *diacetylactis, Lactobacillus casei* subsp. *casei* and *Lactobacillus paracasei* subsp. *paracasei*. Thermophilic lactic acid bacterial species include as examples *Streptococcus thermophilus, Pediococcus acidilactici, Enterococcus faecium, Lactobacillus delbrueckii* subsp. *lactis, Lactobacillus helveticus, Lactobacillus delbrueckii* subsp. *bulgaricus* and *Lactobacillus acidophilus*.

Also the strict anaerobic bacteria belonging to the genus *Bifidobacterium* including *Bifidobacterium bifidum* and *Bifidobacterium longum* are commonly used as dairy starter cultures and are generally included in the group of lactic acid bacteria. Additionally, species of *Propionibacterium* are used as dairy starter cultures, in particular in the manufacture of cheese. Additionally, organisms belonging to the *Brevibacterium* genus are commonly used as food starter cultures.

Another group of microbial starter cultures is fungal cultures, including yeast cultures and cultures of filamentous fungi, which are particularly used in the manufacture of certain types of cheese and beverage. Examples of currently used cultures of fungi include *Penicillium roqueforti, Penicillium candidum, Geotrichum candidum, Torula kefir, Saccharomyces kefir* and *Saccharomyces cerevisiae*.

In the production and storage of fermented food products a persisting problem is the potential contamination of the food material by pathogenic organisms such as *Listeria* spp. In order to overcome this problem the inventors of the present invention surprisingly found that by applying at least one adjunct culture in form of a bacteriocin-producing *Pediococcus* species to the food material it is possible to reduce the amount of pathogenic organisms without influencing the fermentation profile and hence the desired sensorial quality of the food product. This effect is obtained by subjecting the bacteriocin-producing *Pediococcus* species to fermentation conditions that are sub-optimal for growth of the *Pediococcus* species. Typically, such conditions will be optimal for growth of the starter culture and most surprisingly it was found that such conditions allow for a high production of bacteriocin by the *Pediococcus* species. Accordingly, the present invention allows the food manufacturer to select and use the recipes and processing conditions securing optimal development e.g. acidification of the starter culture and at the same time secure optimal food safety by adding the adjunct culture of the present invention at any suitable point in time during the fermentation process.

As mentioned above, the starter culture and the adjunct culture may be added to the food material in any order. The time lapsed between the addition of the first of the starter culture and the adjunct culture to the addition of the second is 0 seconds, e.g. at the most 10 seconds, such as at the most 30 seconds, e.g. at the most 1 minute, such as at the most 5 minutes, e.g. at the most 10 minute, such as at the most 60 minutes, e.g. at the most 300 minute, such as at the most 600 minutes, e.g. at the most 1 day, such as at the most 2 days, e.g. at the most 3 days, such as at the most 4 days, e.g. at the most 6 days.

In a preferred embodiment of the present invention the starter culture is added at the same time or before the adjunct culture is added to the food material.

The invention is successful in reducing and/or inhibiting the amount and/or activity of any pathogenic organism sensitive to bacteriocins produced by *Pediococcus* spp., such as pediocin, in particular *Listeria* spp., such as *Listeria monocytogenes*.

It has been shown that the reduction in pathogenic organisms may be provided by mixing the food material containing the pathogenic organisms with a bacteriocin-producing

*Pediococcus* species. Suitable *Pediococcus* species include *Pediococcus pentosaceus* and *Pediococcus acidilactici*, In particular, the *Pediococcus acidilactici* strain B-LC-20 (DSM 10313) marketed by Chr. Hansen A/S under the trademark SafePro™ is preferred. It is however contemplated that other bacteriocin-producing *Pediococcus* species may provide the same advantageous characteristics and effects as those illustrated herein.

The effect of the bacteriocin-producing *Pediococcus* species is most probably due to the tendency of such *Pediococcus* species to produce bacteriocins capable of killing, inactivating and/or inhibiting pathogenic organisms. Until now it has not been realized that the ability of the *Pediococcus* species to inhibit pathogenic organisms e.g. *Listeria* not necessarily needs to cause a general increase in acidification when added as an adjunct culture. The optimal growth temperature for *Pediococcus* species such as *Pediococcus acidilactici* is about 40° C. or even higher. However, most starter cultures used for food fermentations develop optimally, i.e. result in the desired sensorial quality of the product, at temperatures below 30° C. Thus, previously it was not always suitable to include *Pediococcus* species in order to control e.g. *Listeria* as a reasonable compromise between optimal conditions for the starter vs. optimal conditions for the *Pediococcus* strain could not be established. The present invention will allow the food manufacturer to freely select desired starter culture organisms and perform food fermentation at conditions that are optimal for the desired development of the food product. At the same time the food safety can be secured by adding the adjunct culture of the present invention without adversely influencing the fermentation profile.

Obviously, when it is realized by the skilled person that production of bacteriocin by *Pediococcus* species is not linked to an increase in acidification activity it will be possible to test conditions that favor the bacteriocin production without any significant acid production. Such conditions, with an impact on growth of microbial organisms, are well known by the person skilled in the art. They include but are not limited to water activity, atmospheric conditions, Relative Humidity (RH), nutrients such as carbon source, nitrogen source etc. and other additives such as minerals, vitamins etc. Thus, it is within the scope of the present invention that conditions other than temperature, which is used in the examples provided herein, can be used to obtain a sub-optimal growth of the bacteriocin-producing *Pediococcus* species and thus, obtain the effect of the present invention.

In a preferred embodiment of the present invention the bacteriocin produced by the *Pediococcus* species is selected from the group consisting of Class II bacteriocins, including bacteriocins such as pediocin, bavaracin, sakacin, curvacin, leucosin and plantaricin.

In one aspect, the present invention provides a method (A) for the manufacturing of a fermented food product.

In another aspect, the present invention provides a method (B) for reducing the concentration of *Listeria* spp. in a fermented food product In the present context the term "reducing the concentration" relates to a reduction in the amount of a pathogenic organism. A reduction may be provided by killing, inactivating or inhibiting the activity of the pathogenic organism. In an embodiment of the present invention 100% of the pathogenic organism are killed, inactivated or inhibited, such as at least 90%, e.g. at least 75%, such as at least 50%, e.g. at least 40%, such as at least 30%, e.g. at least 25%, such as at least 20%, e.g. at least 10%, such as at least 5%, e.g. at least 1%.

In certain applications, a "stabilization" of the pathogenic organisms that may be present in the food matrix will be sufficient to render the food safe. Thus, the adjunct culture secures that the pathogenic organisms that are present in the food matrix do not increase in numbers.

Said methods (A and B) comprise the steps of:
(i) providing a food material,
(ii) mixing the food material with a starter culture,
(iii) mixing the food material with at least one adjunct culture in form of a bacteriocin-producing *Pediococcus* species,
(iv) subjecting the mixture provided in step (iii) to a fermentation process, said fermentation process being conducted at conditions that are sub-optimal growth of the bacteriocin-producing *Pediococcus* species in order to provide a limited acidification effect abut allow for a high production of bacteriocin, and obtain the fermented food product.

The fermented food product may be subjected to a drying process simultaneously with the fermentation process in step (iv) and/or subsequent to the fermentation process in step (iv) to obtain a dry fermented food product.

Several food products may be produced by the method according to the present invention provided that the food material is fermented. Examples of fermented food products include, but are not limited to dairy products such as various cheese products, fermented meat product, such as sausages e.g. spreadable and dried sausages and ham, fermented fish and fermented vegetables.

The fermented food product is manufactured by providing a food material which is subjected to a fermentation process and optionally the fermented food product is subjected to a drying process in order to provide a dry fermented food product. In order to reduce the concentration of the pathogenic organisms, it is desired that this reduction can be provided without significantly altering the quality of the final food product, i.e. the food producer may apply the culture to his present or preferred recipe without otherwise changing the recipe or processing conditions.

To obtain the desired effect a culture of bacteriocin-producing *Pediococcus* species is applied to a food material as an adjunct culture, which is separated from the starter culture. In the present context "adjunct culture" is a culture that is added to the food material or joined with the starter culture, but which does not form part of the starter culture, i.e. the adjunct culture is an additional culture not attempted to "produce" the fermented food product, but to supply an extra technological advantage; in this case a killing, inactivating or inhibiting effect towards pathogenic organisms. In the present context "adjunct culture" and "bacteriocin-producing *Pediococcus* species" are used interchangeably and adjunct culture is used to further illustrate the specific characteristics of the bacteriocin-producing *Pediococcus* species.

The manufacturing of the fermented food product is being controlled and performed by the starter culture alone. The starter cultures is responsible for the development of a non-limiting group of quality parameters such as acidification, reduction in water binding and water activity, general appearance, colour, texture, odour, aroma, taste, flavour and other sensorial and technological parameters. Thus, minimal, or preferably no, influence on the quality parameters from the adjunct culture is provided.

In order to limit or eliminate the influence of the bacteriocin-producing *Pediococcus* species on the quality parameters the fermentation process is conducted at conditions sub-optimal for growth of the bacteriocin-producing *Pediococcus* species as described hereinbefore.

In a specific embodiment of the present invention the optional drying process is conducted at conditions that are sub-optimal for growth of the bacteriocin-producing *Pediococcus* species in order to provide a limited acidification effect and allow for a high production of bacteriocin.

In the present context the term "limited acidification" relates to the influence of at least one adjunct culture on acidification. In a preferred embodiment of the present invention the limited acidification provides a difference in pH-value caused by the adjunct culture of 0.5 pH-unit or less, such as 0.25 pH-unit or less, e.g. 0.1 pH-unit or less, such as 0.25 pH-unit or less, e.g. 0.075 pH-unit or less, such as 0.06 pH-unit or less, e.g. 0.05 pH-unit or less, such as 0.04 pH-unit or less, e.g. 0.03 pH-unit or less, such as 0.02 pH-unit or less, e.g. 0.01 pH-unit or less.

In a preferred embodiment of the present invention the sub-optimal growth conditions are provided by changing at least one of the parameters selected from the group consisting of temperature, water activity, RH, atmospheric composition, curing salts, added nutritions, such as the carbon source, additives, such as the chemical acidulant glucono-delta-lactone or various water binding additives and the amounts of bacteria.

In order to provide sub-optimal growth conditions in respect of the adjunct culture during the fermentation process the temperature in the fermentation process is equal to or below 30° C., such as equal to or below 28° C., e.g. equal to or below 26° C., such as equal to or below 24° C.

In order to provide sub-optimal growth conditions during the drying process in respect of the adjunct culture the temperature in the drying process is equal to or below 30° C., such as equal to or below 25° C., e.g. equal to or below 20° C., such as equal to or below 15° C., such as equal to or below 10° C., e.g. equal to or below 5° C.

When mixing the adjunct culture with the food material which either comprises the starter culture or which is subsequently mixed with a starter culture, the concentration of the at least one adjunct culture increases the inoculation level of total lactic acid bacteria at most 1000 times, e.g. at most 500 times, such as at most 100 times, e.g. at most 50 times, such as at most 10 times, e.g. at most 8 times, such as at most 5 times, e.g. at most 4 times, such as at most 3 times, e.g. at most 2 times.

In a preferred embodiment of the present invention the at least one adjunct culture is added in a concentration in the range of $10^2$-$10^{10}$ CFU/g product, e.g. in the range of $10^2$-$10^9$ CFU/g product, such as in the range of $10^3$-$10^9$ CFU/g product, e.g. in the range of $10^4$-$10^9$ CFU/g product, such as in the range of $10^2$-$10^8$ CFU/g product, e.g. in the range of $10^2$-$10^7$ CFU/g product, such as in the range of $10^3$-$10^7$ CFU/g product, e.g. in the range of $10^4$-$10^7$ CFU/g product, such as in the range of $10^5$-$10^7$ CFU/g product, e.g. in the range of $10^6$-$10^7$ CFU/g product such as in the range of $10^3$-$10^6$ CFU/g product, e.g. in the range of $10^3$-$10^5$ CFU/g product, such as in the range of $10^2$-$10^4$ CFU/g product.

In presently preferred embodiment of the invention the adjunct culture is added in a range of $5 \times 10^6$-$9 \times 10^7$ CFU/g product.

In a preferred embodiment of the present invention the food material and/or the dry fermented food product is analysed for the content of pathogenic organisms. If the content of the organisms exceeds a predetermined acceptable level the adjunct culture may be added to the food material in order to kill, inactivate or inhibit the pathogenic organisms.

In the case the food material is analysed for the content of pathogenic organisms and that it is established that the content exceeds a predetermined acceptable level the adjunct culture may be added directly to the food material to kill, inactivate or inhibit the pathogenic organisms.

In the case the dry fermented food product is analysed for the content of pathogenic organisms and that it is established that the content exceeds a predetermined acceptable level, the batches of food materials subsequently produced are mixed with the adjunct culture to kill, inactivate or inhibit the pathogenic organisms.

Under conditions of the method of the invention the bacteriocin-producing *Pediococcus* species can be added to a food fermentation without adversely affecting the fermentation profile. Thus, the species can be used as adjunct cultures for securing microbial safety of fermented food product.

Naturally, the characteristics used to describe the method of the invention will also apply when the strain is used as an adjunct culture as described above.

In specific embodiments, the adjunct culture is provided in a suitable package. Such packages may be e.g. a pouch, a tetra-pak, a can and any other suitable means described in the art for containing microbial species.

Preferably, the package or corresponding marketing material is provided with instructions indicating the fermentation conditions that are sub-optimal for growth of the bacteriocin-producing *Pediococcus* species.

Further, the adjunct culture may be provided in any suitable form e.g. in a frozen or freeze dried form.

In a preferred embodiment the adjunct culture is a freeze-dried preparation of B-LC-20 (DSM 10313) provided by Chr. Hansen A/S under the trademark SafePro™.

The isolated strain is useful for the purposes of the invention described herein. Additionally, it is contemplated that the bacteriocin-producing *Pediococcus* species may be used as a bioprotective agent for improving safety of all food products.

Although, the invention focuses on the application of the adjunct culture during a food fermentation it is within the scope of the present invention that the adjunct culture can be added to a food matrix that are not subjected to a fermentation process.

A sample of the strain has been deposited according to the Budapest Treaty on the International Recognition of the Deposit of Microorganisms for the Purposes of Patent Procedure. The deposit was made on 24 Oct. 1995 under the accession number DSM 10313.

The invention is further illustrated in the following non-limiting examples and in the drawings, where.

EXAMPLES

Example 1

Influence of B-LC-20 on pH Development in Sausage Mince.

The influence of the adjunct culture on acidification is demonstrated and a summary of the pH/time profiles encountered when applying B-LC-20 to sausage mince. Table 1 shows the pH development during the fermentation period as determined every second day and table 2 shows the pH development as determined continuously from 0 to 68 hours.

TABLE 1 pH development in sausage mince determined each second day

| Code | Day 0 | Day 2 | Day 4 | Day 6 |
| --- | --- | --- | --- | --- |
| Control (starter culture) | 5.79 ± 0.04 | 4.81 ± 0.03 | 4.80 ± 0.04 | 4.79 ± 0.01 |
| Control + B-LC-20 | 5.79 ± 0.01 | 4.77 ± 0.01 | 4.77 ± 0.01 | 4.80 ± 0.04 |

TABLE 2 pH development in sausage mince determined by continuous measurement

| | Code/Hours | | | | | | | |
| --- | --- | --- | --- | --- | --- | --- | --- | --- |
| | 0 | 10 | 20 | 30 | 40 | 50 | 60 | 68 |
| Control (starter culture) | 5.62 | 5.71 | 5.58 | 5.16 | 4.97 | 4.86 | 4.79 | 4.77 |
| Control + B-LC-20 | 5.62 | 5.70 | 5.55 | 5.12 | 4.91 | 4.80 | 4.76 | 4.76 |

The results show that there is no significant influence on the final pH of adding the adjunct culture in form of B-LC-20 together with the control culture as compared to adding the control culture alone. B-LC-20 was added in a concentration of $1.1 \times 10^7$ CFU/g mince. Control culture was added in a total lactic acid bacteria concentration of $3.3 \times 10^6$ CFU/g.

It is shown that there is a slight influence of B-LC-20 during the first 20-60 hours, but the maximum difference between the two curves is 0.06 pH-unit which is well within the normal batch to batch variation encountered in real sausage productions.

The control starter culture consists of a blend of lactobacilli, pediococci, micrococci and staphylococci.

Example 2

Influence of B-CL-20 on *Listeria* Reduction
Summary of Trials

Two independent trials to assess the behavior of *Listeria* in sausages along the ripening process were performed. Three batches were manufactured in each trial. One with the control starter culture non active against *Listeria* and two batches with the control starter culture together with an antilisteria starter culture added at two different concentrations (B-LC-20, Chr. Hansen A/S). Each batch was inoculated with a cocktail of five *Listeria monocytogenes* strains (approx. $10^3$ CFU/g) at the time of manufacturing.

Ripening was done in an adapted versatile environment test chamber Sanyo Model MLR-350H, with a fermentation period for 72 h at 14° C. with 80% RH.

At the selected times three sausages were sampled from each batch for determining *Listeria* and Lactic acid Bacteria counts, pH and weight loss.

The behavior of *Listeria* was similar in both trials, showing important differences between the control batch (A) and the batch added the antilisteria containing cultures (B and C) where *Listeria* diminished 2 log cfu/g (trial 1) and 3 log cfu/g in trial 2. No significant differences in the *Listeria* counts between batches B and C were observed.

In conclusion the above result points out that the bacterial culture B-LC-20 proved to be a suitable culture for sausages manufactured according to the present formulation, showing additional *Listeria* reduction after the fermentation period and till the end of the ripening as compared to the control starter culture alone.

Methodology

A *Listeria* challenge test in dry sausages along the ripening process was designed according to the following protocol. Two independent trials (trial 1 and trial 2) were performed at Institut de Recerca I Tecnologia Agroalimentáries (IRTA), Monells, Spain. The anti-*Listeria* activity of the Lactic acid Bacteria culture B-LC-20 at two different concentrations were tested.

Bacterial Cultures

Chr. Hansen anti.*listeria* culture B-LC-20 and the control starter culture was stored frozen (−20° C.) until use.

*Listeria monocytogenes*: Two strains were from the strain collection of IRTA, i.e. strain CTC1011 and CTC1034; and three strains were supplied by Chr. Hansen (P01, P05, P15). Each strain was separately grown in the IRTA standard medium "TSBYE" and stored frozen (−20° C.). Viable counts were determined before each trial in order to calculate the appropriate dilution to reach the expected inoculation in the meat mixture (approximately $10^3$ CFU/g).

Manufacturing

Three batches (12 Kg each) were manufactured.

Batch A Control (starter culture)+*Listeria monocytogenes* cocktail

Batch B Control (starter culture)+B-LC-20 low concentration

Batch C Control (starter culture)+B-LC-20 high concentration

The bacterial cultures were added separately at the time of mixing. First was added *L. monocytogenes* cocktail (in 20 ml saline solution), followed by the starter culture and the adjunct culture.

Ripening Conditions

Fermentation and drying of sausages were done in an adapted versatile environmental test chamber Sanyo Model MLR-350H.

Fermentation was carried out for 72 h at 24° C. with RH>90%.

After the fermentation period the conditions were adjusted for drying until day 29 at 14° C. with 80% RH.

Analyses

During fermentation and drying, pH and weight loss were measured in 3 marked sausages per batch, daily during the first week and with an interval of 3-4 days during the last 3 weeks.

Microbial Analyses

Three different sausages from each batch (A, B, C) were nalaysed at each sampling time (days: zero (after 4 hours), 2, 7, 14 and 29). Each sample consisted of 25 grams of a previous homogenized sausage.

The determination of *Listeria* was done at each sampling time, except at day 0, by Most Probably Number technique (MPN) in Fraser Broth Base (Oxoid)+Half Fraser selective supplement (Oxoid) (48 hours, 37° C.) followed by confirmation of the positive tubes in Palcam *Listeria* Selective Agar Base (Merck)+Selective Supplement att. Van Netten et al. (Merck) (48 hours, 37° C.).

*Listeria* counts at time zero were done by spreading the appropriate dilutions in Palcam supplemented agar plates and incubating at 37° C. for 72 hours. Lactic acid bacteria counts were performed at each sampling time in MRS agar (72 hours at 30° C. under anaerobic conditions).

TABLE 1

*Listeria* spp. And Lactic Acid Bacteria counts along the ripening of dry sausages in trial 1.

| Batch | Time (days) | *Listeria* spp. | Lactic Acid Bacteria |
|---|---|---|---|
| A | 0 | 3.31 ± 0.02 | 6.47 ± 0.11 |
| A | 2 | 2.69 ± 0.33 | 8.85 ± 0.05 |
| A | 7 | 3.15 ± 0.19 | 8.93 ± 0.07 |
| A | 14 | 2.45 ± 0.18 | 8.73 ± 0.06 |
| A | 29 | 2.34 ± 0.35 | 8.60 ± 0.01 |
| B | 0 | 3.25 ± 0.04 | 7.50 ± 0.06 |
| B | 2 | 2.24 ± 0.12 | 8.73 ± 0.08 |
| B | 7 | 1.77 ± 0.35 | 8.78 ± 0.17 |
| B | 14 | 1.18 ± 0.39 | 8.61 ± 0.03 |
| B | 29 | 0.89 ± 0.69 | 8.51 ± 0.02 |
| C | 0 | 3.22 ± 0.10 | 7.77 ± 0.05 |
| C | 2 | 2.05 ± 0.41 | 8.68 ± 0.07 |
| C | 7 | 1.48 ± 0.26 | 8.75 ± 0.20 |
| C | 14 | 1.43 ± 0.51 | 8.52 ± 0.04 |
| C | 29 | 0.54 ± 0.16 | 8.41 ± 0.09 |

Values are the average of triplicate samples expressed as log cfu/g standard deviation.

Batches were inoculated as follows:

Batch A (control starter culture, $3.0\times10^6$ CFU/g), Batch B (control starter culture+B-LC-20 low concentration ($2.9\times10^7$ CFU/g mince)), Batch C (control starter culture+B-LC-20 high concentration ($5.6\times10^7$ CFU/g mince)).

All the batches were inoculated with a cocktail of 5 different *Listeria monocytogenes* strains (CTC1011, CTC1034, P01, P05, P15).

TABLE 2 pH and weight loss along the ripening of dry sausages in trial 1.

| Batch | Time (days) | pH | Weight loss % |
|---|---|---|---|
| A | 0 | 5.82 ± 0.01 | NA |
| A | 1 | 5.57 ± 0.04 | 1.54 ± 0.73 |
| A | 2 | 4.90 ± 0.09 | 2.96 ± 1.49 |
| A | 3 | 4.67 ± 0.04 | 5.79 ± 1.13 |
| A | 4 | 4.60 ± 0.01 | 10.36 ± 0.79 |
| A | 7 | 4.69 ± 0.01 | 17.04 ± 0.60 |
| A | 11 | 4.75 ± 0.01 | 21.66 ± 0.54 |
| A | 14 | 4.71 ± 0.01 | 24.31 ± 0.34 |
| A | 18 | 4.86 ± 0.02 | 27.04 ± 0.38 |
| A | 24 | 4.75 ± 0.01 | 30.23 ± 0.33 |
| A | 29 | 4.99 ± 0.13 | 31.89 ± 0.36 |
| B | 0 | 5.79 ± 0.03 | NA |
| B | 1 | 5.50 ± 0.05 | 1.22 ± 0.64 |
| B | 2 | 4.92 ± 0.01 | 2.46 ± 0.76 |
| B | 3 | 4.61 ± 0.03 | 4.24 ± 0.74 |
| B | 4 | 4.49 ± 0.01 | 8.71 ± 1.15 |
| B | 7 | 4.55 ± 0.02 | 15.92 ± 0.71 |
| B | 11 | 4.58 ± 0.01 | 21.71 ± 0.33 |
| B | 14 | 4.49 ± 0.17 | 25.02 ± 0.65 |
| B | 18 | 4.69 ± 0.01 | 28.36 ± 0.39 |
| B | 24 | 4.63 ± 0.01 | 31.27 ± 0.58 |
| B | 29 | 4.75 ± 0.01 | 32.89 ± 0.61 |
| C | 0 | 5.83 ± 0.01 | NA |
| C | 1 | 5.37 ± 0.01 | 1.32 ± 0.49 |
| C | 2 | 4.89 ± 0.03 | 2.67 ± 0.53 |
| C | 3 | 4.59 ± 0.02 | 5.104.89 ± 0.03 |
| C | 4 | 4.49 ± 0.01 | 9.66. ± 0.33 |
| C | 7 | 4.55 ± 0.01 | 16.69. ± 0.26 |
| C | 11 | 4.61 ± 0.01 | 22.57 ± 0.30 |
| C | 14 | 4.57 ± 0.02 | 25.57 ± 0.28 |
| C | 18 | 4.69 ± 0.01 | 28.60 ± 0.07 |
| C | 24 | 4.62 ± 0.01 | 31.56 ± 0.25 |
| C | 29 | 4.74 ± 0.03 | 33.15 ± 0.26 |

NA = non applicable
Values are the average of triplicate samples ± standard deviation.

TABLE 3

*Listeria* spp. and Lactic Acid Bacteria counts along the ripening of dry sausages in trial 2.

| Batch | Time (days) | *Listeria* spp. | Lactic Acid Bacteria |
|---|---|---|---|
| A | 0 | 3.40 ± 0.01 | 6.41 ± 0.15 |
| A | 2 | 2.56 ± 0.54 | 8.83 ± 0.04 |
| A | 7 | 2.68 ± 0.36 | 8.75 ± 0.04 |
| A | 14 | 1.86 ± 0.19 | 8.76 ± 0.03 |
| A | 29 | 1.56 ± 0.35 | 8.39 ± 0.14 |
| B | 0 | 3.39 ± 0.03 | 7.25 ± 0.07 |
| B | 2 | 2.04 ± 0.12 | 8.56 ± 0.10 |
| B | 7 | 1.13 ± 0.26 | 8.58 ± 0.11 |
| B | 14 | 1.16 ± 0.20 | 8.35 ± 0.08 |
| B | 29 | 0.33 ± 0.17 | 8.33 ± 0.08 |
| C | 0 | 3.67 ± 0.05 | 7.79 ± 0.02 |
| C | 2 | 1.87 ± 0.19 | 8.50 ± 0.08 |
| C | 7 | 1.56 ± 0.35 | 8.47 ± 0.07 |
| C | 14 | 0.84 ± 0.20 | 8.52 ± 0.12 |
| C | 29 | 0.23 ± 0.23 | 8.34 ± 0.04 |

Values are the average of triplicate samples as log cfu/g standard deviation.

Batch A (control starter culture, $2.6\times10^6$ CFU/g), Batch B (control starter culture+B-LC-20 low concentration ($1.5\times10^7$ CFU/g), Batch C (control starter culture+B-LC-20 high concentration ($5.9\times10^7$ CFU/g).

All the batches were inoculated with a cocktail of 5 different *Listeria monocytogenes* strains (CTC1011, CTC1034, P01, P05, P15).

TABLE 4 pH and weight loss along the ripening of dry sausages in trial 2.

| Batch | Time (days) | PH | Weight loss % |
|---|---|---|---|
| A | 0 | 6.10 ± 0.07 | NA |
| A | 1 | 5.83 ± 0.02 | 3.09 ± 1.27 |
| A | 2 | 5.04 ± 0.03 | 4.73 ± 1.13 |
| A | 3 | 4.86 ± 0.03 | 7.30 ± 1.39 |
| A | 4 | 4.90 ± 0.01 | 10.03 ± 0.89 |
| A | 7 | 4.91 ± 0.01 | 14.81 ± 0.76 |
| A | 11 | 4.95 ± 0.01 | 19.19 ± 0.53 |
| A | 14 | 4.94 ± 0.01 | 21.14 ± 0.48 |

TABLE 4-continued pH and weight loss along the ripening of dry sausages in trial 2.

| Batch | Time (days) | PH | Weight loss % |
|---|---|---|---|
| A | 18 | 4.98 ± 0.01 | 24.08 ± 0.66 |
| A | 24 | 5.04 ± 0.01 | 27.41 ± 0.44 |
| A | 29 | 5.04 ± 0.01 | 29.92 ± 0.43 |
| B | 0 | 5.97 ± 0.02 | NA |
| B | 1 | 5.52 ± 0.07 | 3.79 ± 1.48 |
| B | 2 | 4.98 ± 0.02 | 5.17 ± 1.03 |
| B | 3 | 4.72 ± 0.03 | 7.90 ± 1.70 |
| B | 4 | 4.72 ± 0.01 | 11.31 ± 1.06 |
| B | 7 | 4.71 ± 0.03 | 16.53 ± 0.95 |
| B | 11 | 4.74 ± 0.01 | 21.84 ± 0.38 |
| B | 14 | 4.75 ± 0.01 | 23.96 ± 0.39 |
| B | 18 | 4.80 ± 0.02 | 27.24 ± 0.40 |
| B | 24 | 4.84 ± 0.02 | 30.90 ± 0.20 |
| B | 29 | 4.89 ± 0.02 | 33.26 ± 0.13 |
| C | 0 | 5.99 ± 0.01 | NA |
| C | 1 | 5.49 ± 0.04 | 2.77 ± 0.59 |
| C | 2 | 4.93 ± 0.01 | 4.16 ± 1.16 |
| C | 3 | 4.68 ± 0.01 | 6.33 ± 0.75 |
| C | 4 | 4.70 ± 0.01 | 9.985 ± 0.48 |
| C | 7 | 4.68 ± 0.02 | 15.84 ± 0.60 |
| C | 11 | 4.70 ± 0.01 | 21.29 ± 0.61 |
| C | 14 | 4.74 ± 0.01 | 23.52 ± 0.51 |
| C | 18 | 4.79 ± 0.02 | 26.65 ± 0.62 |
| C | 24 | 4.84 ± 0.02 | 30.37 ± 0.58 |
| C | 29 | 4.83 ± 0.02 | 32.69 ± 0.67 |

NA = non applicable
Values are the average of triplicate samples ± standard deviation.

Discussion

Two independent trials to assess the behavior of *Listeria* in sausages along the ripening process were performed. Three batches were manufactured in each trial. One control with starter culture non active against *listeria* and two batches with the same starter culture plus an antilisteria adjunct culture added at two different concentrations (B-LC-20) in each batch. Each batch was inoculated with a cocktail of five *Listeria monocytogenes* strains (approx. 103 cfu/g) at the time of manufacturing.

In both trials and after 2 days of fermentation *Listeria* diminished. The counts in batch B and C were lower than in batch A. These differences between the control batch A and the batches inoculated with the antilisterial cultures increased until the end of ripening. In trial 1, by the end of the ripening, *Listeria* diminished 1 log cfu/g in batch A while in batch B and C *Listeria* decreased more than 2 logs cfu/g. In trial 2 by the end of ripening *Listeria* diminished 1.8 (log cfu/g) in batch A, and more than 3 logs in batch B and C.

Lactic acid bacteria counts reached the maximum after 2 days of fermentation with similar values at the end of the process in each batch (around 108 cfu/g) in both trials. The curve of pH was similar for the different batches in both trials. The minimum pH was recorded after 4 days in trial 1 and after 3 days in trial 2 despite the pH at time zero was higher in trial 2. The pH-drop in the control batches were in both trials similar to the pH-drop in the batch with added adjunct culture. ΔpH was between 1.22-1.24 in batch A after 3-4 days of fermentation, and between 1.26-1.34 in batches B and C. The small differences were probably caused by the extra glucose added with the adjunct culture pouch. Weight loss showed similar profile in both trials with no differences between the lots.

Conclusion

The culture B-LC-20 proved to be a suitable protective adjunct culture for fermented sausages manufactured according to the present formulation, showing additional *Listeria* reduction after the fermentation period and till the end of ripening, compared to a control starter culture alone.

In general, addition of extra inoculum of lactic acid bacteria reduces the time to on-set of fermentation (the lag phase) and thereby speed up the overall acidification rate. When increasing the inoculum by 10 times (from $5 \cdot 10^5$ to $5 \cdot 10^6$ CFU/g) acidification lag phase for a typical North European type fermented sausage was halfed and the time to reach pH of 5.3 and 4.9 reduced by 25 and 30%, respectively.

Addition of B-LC-20 to the sausage recipe in Example 2, trial 1 resulted in increased inoculation level of total lactic acid bacteria of approx. 15 times, from $3 \cdot 10^6$ to between $3 \cdot 10^7$-$6 \cdot 10^7$. It was expected that the lag phase would have been reduced considerably and the time to reach pH 4.9 reduced by at least 30%. This expected reduction did not take place, pH reached 4.9 after 2 days for all three batches, i.e. addition of an adjunct culture such as B-LC-20 to the existing recipe did not speed up acidification time as expected. In example 1, table 1 and 2 acidification speed did not increase significantly, either.

Therefore, the inventors of the present invention surprisingly found that the use of an adjunct culture such as B-LC-20 provides a unique anti-listerial reduction for fermented sausages since it was found that *Pediococcus acidilactici* is a strong producer of pediocin (which destroys *Listeria monocytogenes*) at European fermentation temperatures (<26° C.) while not being a strong acidifier at this temperature.

The reduction of *Listeria* is primarily caused by pediocin produced by an adjunct culture such as B-LC-20 in the food material during the fermentation and drying process. The effect of pediocin is a well known phenomenon in the literature.

However, the uniqueness of the adjunct culture (B-LC-20) and the method disclosed herein is that the food manufacturer can use the adjunct culture together with the normal acidification culture since it does not alter the overall acidification profile and the quality of the product significantly. As mentioned above, the acidification profile is of utmost importance for the sensory quality. Thus, the manufacturer does not need to change his present recipe or processing conditions, but will get the advantage of reduction in *Listeria* numbers.

Example 3

Figure 1A:
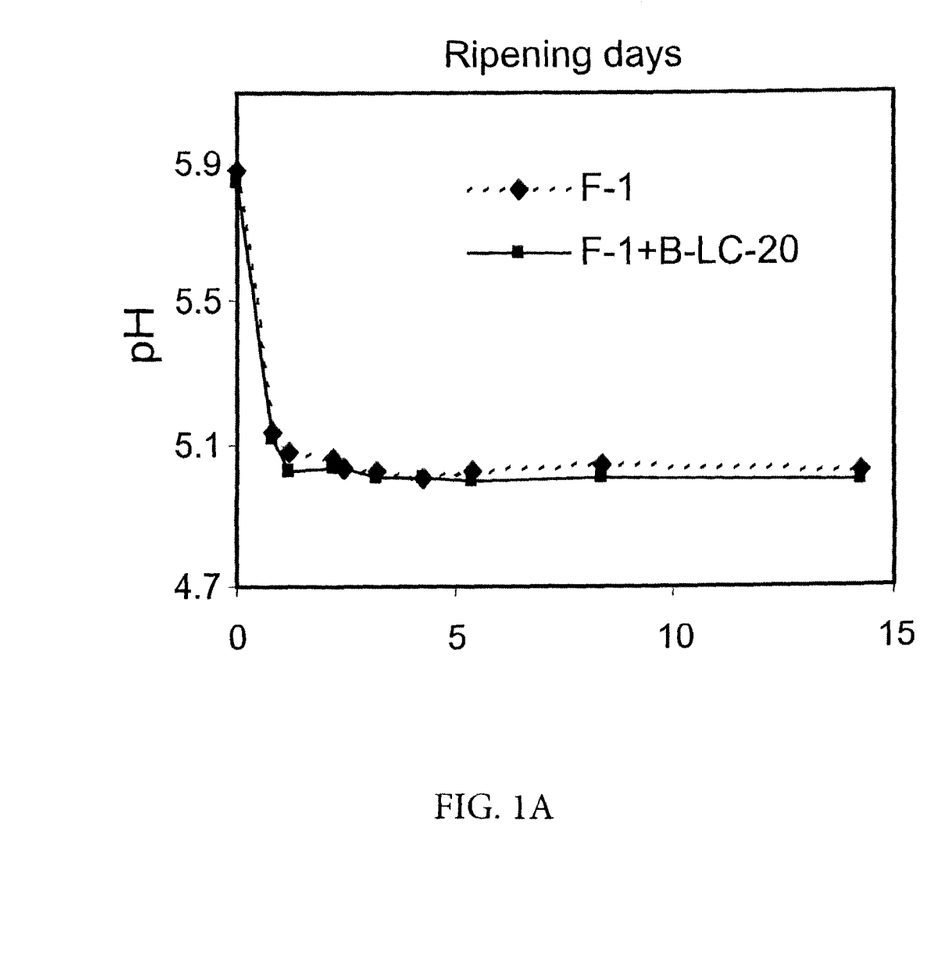
FIG. 1A illustrates the pH-development during ripening of sausages applied with or without B-LC-20 together with a Chr. Hansen BACTOFERM™ fast fermenting starter culture F1. Sausages were fermented at 24-20° C. for 3 days, followed by ripening at 18 to 16° C. for 11 days.
Figure 1B:
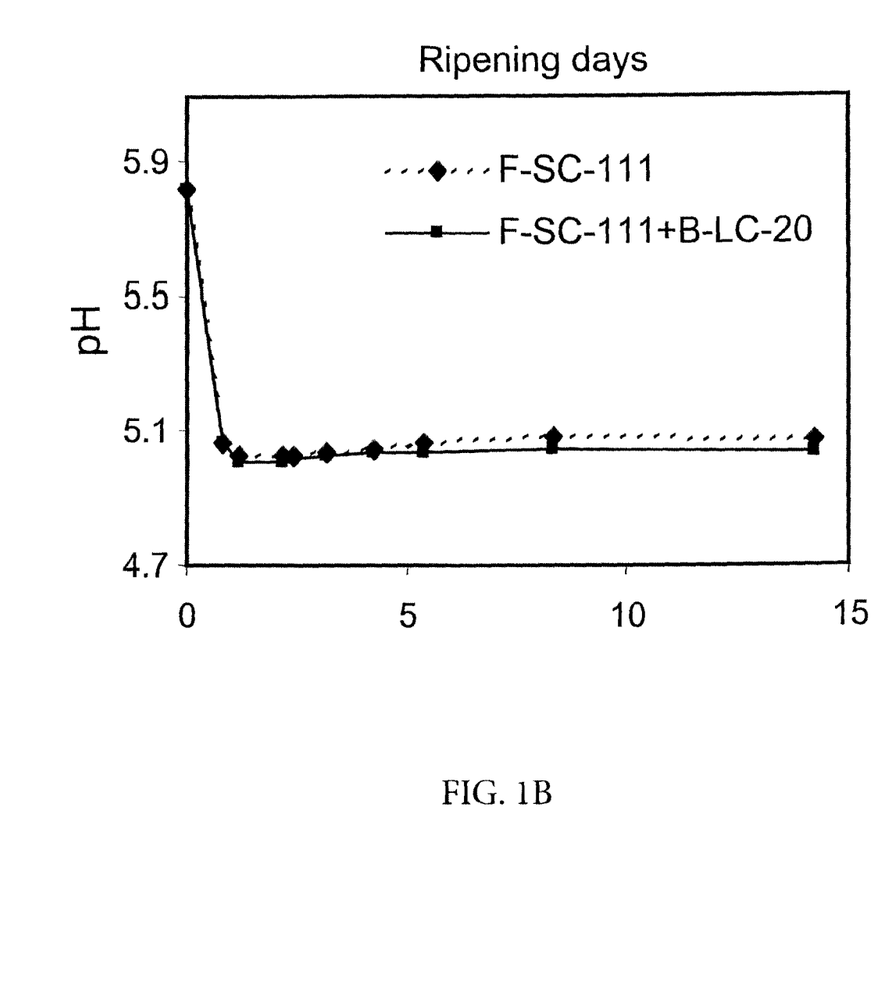
FIG. 1B illustrates the pH-development during ripening of sausages applied with or without B-LC-20 together with a Chr. Hansen BACTOFERM™ fast fermenting starter culture F-SC-111. Sausages were fermented at 24-20° C. for 3 days, followed by ripening at 18 to 16° C. for 11 days.
Figure 2A:
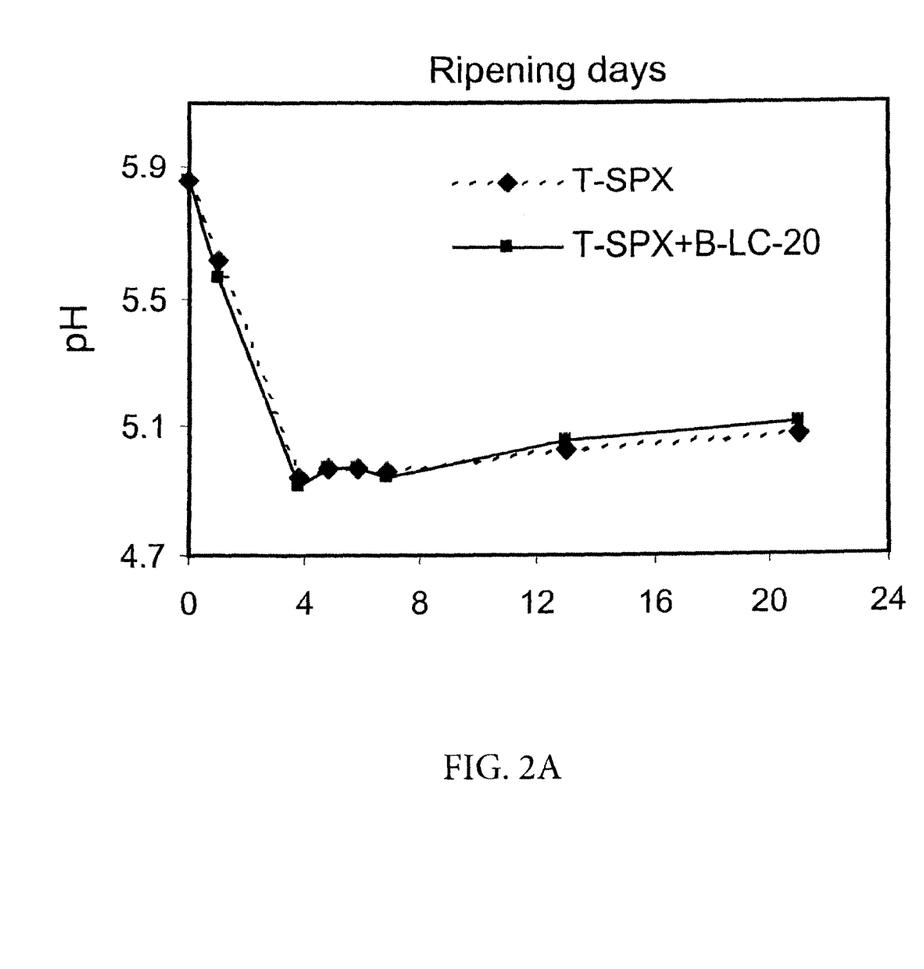
FIG. 2A illustrates pH-development during ripening of sausages applied with or without B-LC-20 together with a Chr. Hansen BACTOFERM™ traditional fermenting starter culture T-SPX. Sausages were fermented at 24-20° C. for 4 days, followed by ripening at 18 to 14° C. for 17 days.
Figure 2B:
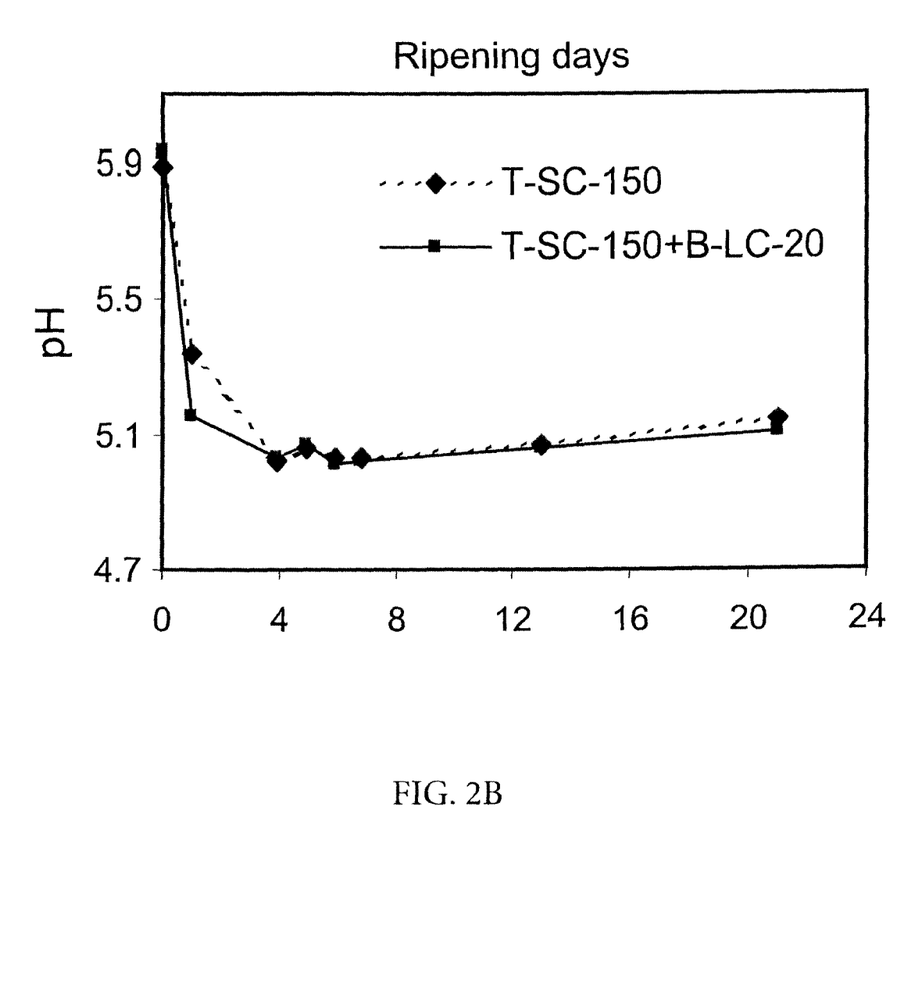
FIG. 2B illustrates pH-development during ripening of sausages applied with or without B-LC-20 together with a Chr. Hansen BACTOFERM™ traditional fermenting starter culture T-SC-150. Sausages were fermented at 24-20° C. for 4 days, followed by ripening at 18 to 14° C. for 17 days.

Influence of the Adjunct Culture on the Acidification Profile of Different Fermented Sausages The influence of the adjunct culture B-LC-20 on the acidification profile of four types of sausages fermented with different starter cultures are demonstrated in FIGS. 1 and 2. In all cases, the addition of the adjunct culture in the sausage mince together with the starter culture did not influence the acidification profile of the sausages significantly. In addition, internal sensory evaluations showed that the sensory quality of the sausages was unchanged by addition of B-LC-20.

|  | Organisms | Inoculation, total LAB |
|---|---|---|
| F-1 | *Pediococcus pentosaceus* *Staphylococcus xylosus* | $5 \times 10^6$ CFU/g mince |
| F-SC-111 | *Lactobacillus sakei* *Staphylococcus carnosus* | $1 \times 10^7$ CFU/g mince |
| T-SPX | *Pediococcus pentosaceus* *Staphylococcus xylosus* | $5.5 \times 10^6$ CFU/g mince |
| T-SC-150 | *Lactobacillus sakei* *Staphylococcus carnosus* | $1 \times 10^7$ CFU/g mince |

LITERATURE

Foegeding, P. M.; Thomas, A. B.; Pilkington, D. H.; Klaenhammer, T. R. 1992. *"Enhanced control of Listeria monocytogenes by in situ-produced pediocin during dry fermented sausage production"*, Applied and Environmental Microbiology, Vol. 58(3), page 884-890.

Tjener, K., Stahnke, L. H., Andersen, L., Martinussen, J. 2003. *"A fermented meat model system for studies of microbial aroma formation"*. Meat Science, 66(1), 211-218.

Utility model BA 1994 00266

The invention claimed is:

1. A fermented food product produced by a method comprising:
   (i) mixing a food material with (a) a starter culture and (b) at least one adjunct culture comprising *Pediococcus acidilactici* that produces a bacteriocin;
   (ii) fermenting the food material at a sub-optimal temperature for growth of the *Pediococcus acidilactici* of 30° C. or below; and
   (iii) ripening the food material;
   wherein during fermentation the acidification caused by the *Pediococcus acidilactici* is about 0.5 pH unit or less, and wherein growth of *Listeria monocytogenes* during fermentation and/or ripening is suppressed, and wherein the pH of the fermented food product is at most 0.5 pH units lower than that of a fermented food product produced by the same method except without the *Pediococcus acidilactici* adjunct culture.

2. The fermented food product of claim 1, wherein the bacteriocin is selected from the group consisting of pediocin, bavaracin, sakacin, curvacin, leucosin, and plantaracin.

3. The fermented food product of claim 1, wherein at least 75% of the *L. monocytogenes* are killed, inactivated, or inhibited by the end of ripening.

4. The fermented food product of claim 1, wherein the method further comprises a drying process performed under sub-optimal conditions for growth of the *P. acidilactici*.

5. The fermented food product of claim 1, wherein the fermenting is performed under further sub-optimal growth conditions for the *P. acidilactici* provided by at least one parameter selected from water activity, relative humidity, atmospheric composition, curing salts, added nutrients, and other additives.

6. The fermented food product of claim 1, wherein the method reduces counts of *Listeria monocytogenes* by at least 2 log cfu/g of fermented food by the end of ripening.

7. The fermented food product of claim 1, wherein the fermented food product is selected from the group consisting of cheese, sausage, ham, fish, and vegetables.

8. The fermented food product of claim 1, wherein the fermented food product is sausage.

9. A fermented food product produced by a method comprising:
   (i) mixing a food material with (a) a starter culture and (b) at least one adjunct culture comprising *Pediococcus acidilactici* that produces a bacteriocin and
   (ii) fermenting the food material at a sub-optimal temperature for growth of the *Pediococcus acidilactici* of 30° C. or below,
   wherein during fermentation the acidification caused by the *Pediococcus acidilactici* is about 0.5 pH unit or less, and wherein growth of *Listeria monocytogenes* during fermentation is suppressed, and
   wherein the pH of the fermented food product is at most 0.5 pH units lower than that of a fermented food product produced by the same method except without the *Pediococcus acidilactici* adjunct culture.

10. The fermented food product of claim 9, wherein the bacteriocin is selected from the group consisting of pediocin, bavaracin, sakacin, curvacin, leucosin, and plantaracin.

11. The fermented food product of claim 9, wherein at least 75% of the *L. monocytogenes* are killed, inactivated, or inhibited by the end of ripening.

12. The fermented food product of claim 9, wherein the method further comprises a drying process performed under sub-optimal conditions for growth of the *P. acidilactici*.

13. The fermented food product of claim 9, wherein the fermenting is performed under further sub-optimal growth conditions for the *P. acidilactici* provided by at least one parameter selected from water activity, relative humidity, atmospheric composition, curing salts, added nutrients, and other additives.

14. The fermented food product of claim 9, wherein the method reduces counts of *Listeria monocytogenes* by at least 2 log cfu/g of fermented food by the end of ripening.

15. The fermented food product of claim 9, wherein the fermented food product is selected from the group consisting of cheese, sausage, ham, fish, and vegetables.

16. The fermented food product of claim 9, wherein the fermented food product is sausage.

17. A method for producing a fermented food product, comprising:
   fermenting a food material with at least one adjunct culture comprising *Pediococcus acidilactici* that produces bacteriocin, wherein during fermentation the acidification caused by the *Pediococcus acidilactici* is about 0.5 pH units or less.

* * * * *